United States Patent [19]
Antonini et al.

[11] Patent Number: 5,814,717
[45] Date of Patent: Sep. 29, 1998

[54] OIL SEAL TESTER

[75] Inventors: Joseph Antonini, Chicago, Ill.; Mark Shuster, Sylvania, Ohio; David Sverdlik, Morton Grove, Ill.

[73] Assignee: Dana Corporation, Toledo, Ohio

[21] Appl. No.: 777,662

[22] Filed: Dec. 31, 1996

[51] Int. Cl.[6] .................................................. G01N 3/56
[52] U.S. Cl. .................................................................. 73/9
[58] Field of Search .................................. 73/7, 9, 10, 47, 73/49.8, 40, 862.541, 862.543; 277/2

[56] References Cited

U.S. PATENT DOCUMENTS

| | | |
|---|---|---|
| 2,486,280 | 10/1949 | Hausmann ...................................... 73/9 |
| 3,167,964 | 2/1965 | Dega et al. . |
| 3,176,497 | 4/1965 | Dega ............................................. 73/9 |
| 3,313,141 | 4/1967 | Jagger et al. ................................. 73/9 |

*Primary Examiner*—Robert Raevis
*Attorney, Agent, or Firm*—Rader, Fishman & Grauer PLLC

[57] ABSTRACT

An oil seal tester having a moving shaft for engaging an oil sealing surface of a oil seal and at least one source of fluid to be applied against the moving shaft and against a first side of the oil seal. A force measuring device is used to measure the reaction torque exerted against the seal by the rotating shaft. Adjustments are provided for altering the shaft to bore misalignment and the run out of the rotating shaft.

15 Claims, 3 Drawing Sheets

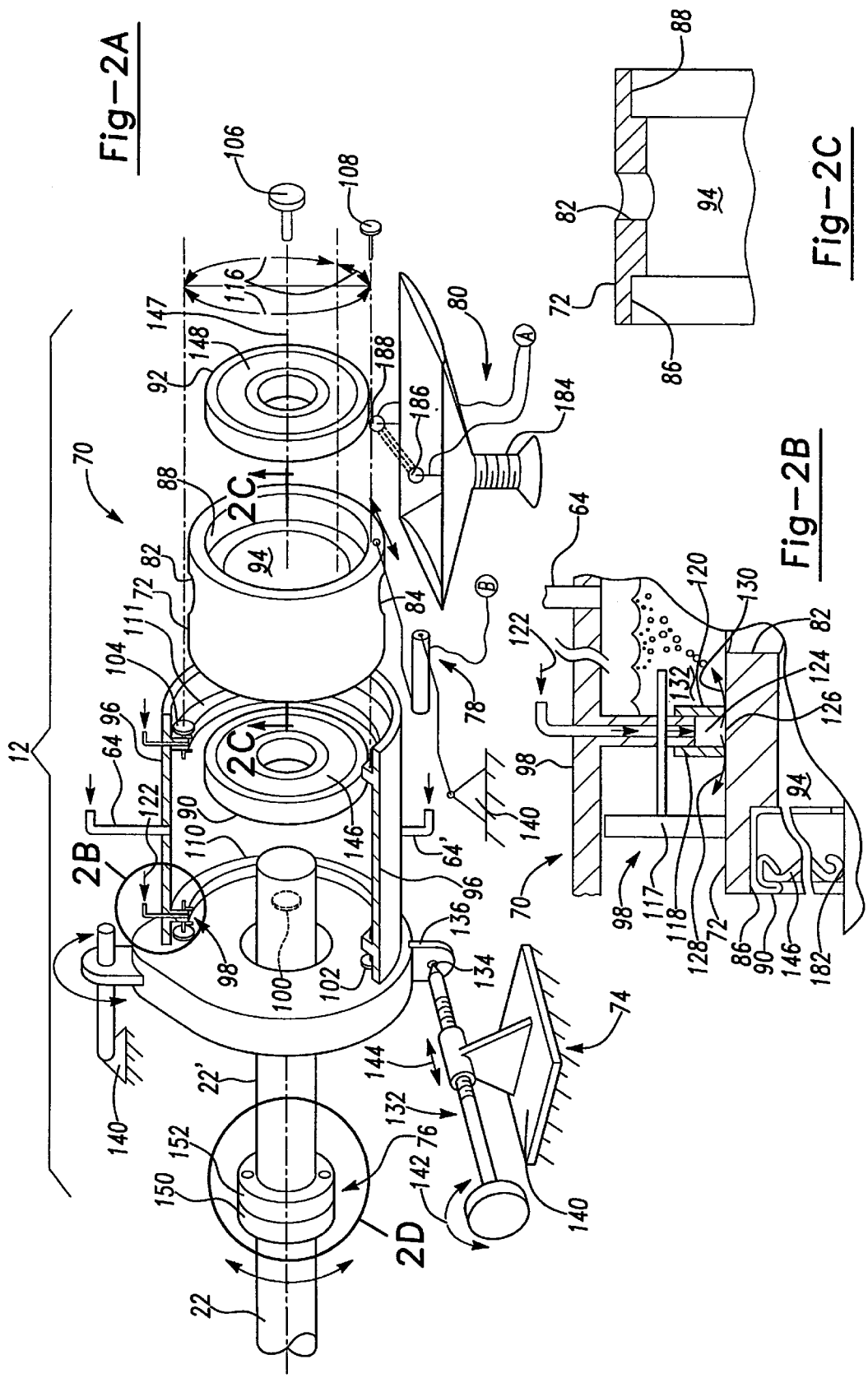

OIL SEAL TESTER

TECHNICAL FIELD

This invention relates to testing devices and more particularly relates to devices for testing the integrity and durability of oil seals.

BACKGROUND OF THE INVENTION

Oil seals are commonly employed in many applications which require that a fluid (primarily lubricating oil) be prevented from migrating along a moving shaft. In general, a lip-type seal is used in such a capacity in automotive applications. Lip type seals generally are constructed using an outer metallic casing within which an elastomer annulus is secured. A radially innermost portion of the elastomer member is formed into a flexible lip to be placed in wiping engagement with a moving shaft extending through the annulus of the elastomer. Conventional lip-type seals are generally provided with a mechanical spring encircling the flexible lip portion of the elastomer to ensure proper engagement of the flexible lip against the moving shaft.

In order to ensure that a particular seal design will not leak within its rated lifetime and that it will meet other durability criterion, seals are often tested. Testing of seals can take place in one of two ways—they can either be tested after being assembled to the actual equipment they are designed to be used on or they can be tested using a seal test machine. Seal test machines are generally known (see U.S. Pat. No. 3,167,964) and generally include a shaft moved by a motor. The shaft is sized to the same dimension as the shaft on which the seal will ultimately be coupled. Most of the prior art sealing devices include some means for determining the quality of the fluid seal achieved by the seal against the moving shaft.

Although the prior art oil seal test devices do appear to be operative for their intended purposes, they fall short in providing a full array of test conditions which simulate the actual conditions oil seals used in automotive applications typically experience. For example, it is not uncommon for an oil seal used in automotive applications to experience a wide variance in temperature. Also, many automotive applications subject the oil seal to certain misalignments such as shaft to bore misalignment and shaft out of round condition. If these particular conditions cannot be simulated by an oil test machine, the results generated by a test conducted by such an oil test machine are of questionable value.

Thus it is an object of this invention to provide an oil test machine which allows the temperature, shaft to bore misalignment, and shaft round conditions to be varied.

It is still a further object of this invention to provide an oil seal test machine which measures the amount of torque imparted from the rotating shaft to the oil seal being tested.

SUMMARY OF THE INVENTION

The oil seal tester of the present invention includes a moving shaft for engaging an oil sealing surface of an oil seal. Also included is at least one source of fluid to be applied against the moving shaft and against the first side of said oil seal. A force measuring device is attached to the oil seal housing for measuring the force imparted to the oil seal from said moving shaft.

In a preferred embodiment, the oil seal tester includes means for heating and cooling the source of fluid and also mechanisms for adjusting shaft run out and shaft to bore misalignment. Two devices are set forth for detecting the passage of fluid beyond the sealing surface of the seal. These include a volumetric measurement device and a drop detection device.

Preferably, Teflon® sealing rings are used in conjunction with pressurized air to provide a low friction seal between members of the oil seal tester so that the force measuring device is not prone to errors induced by friction.

BRIEF DESCRIPTION OF THE DRAWINGS

FIG. 2A is an exploded view of the oil seal head assembly.

FIG. 2B is an enlarged view of encircled portion B of FIG. 2A.

FIG. 2C is a partial cross sectional view taken substantial through line C—C of FIG. 2A.

DETAILED DESCRIPTION OF THE PREFERRED EMBODIMENTS

Figure 1:
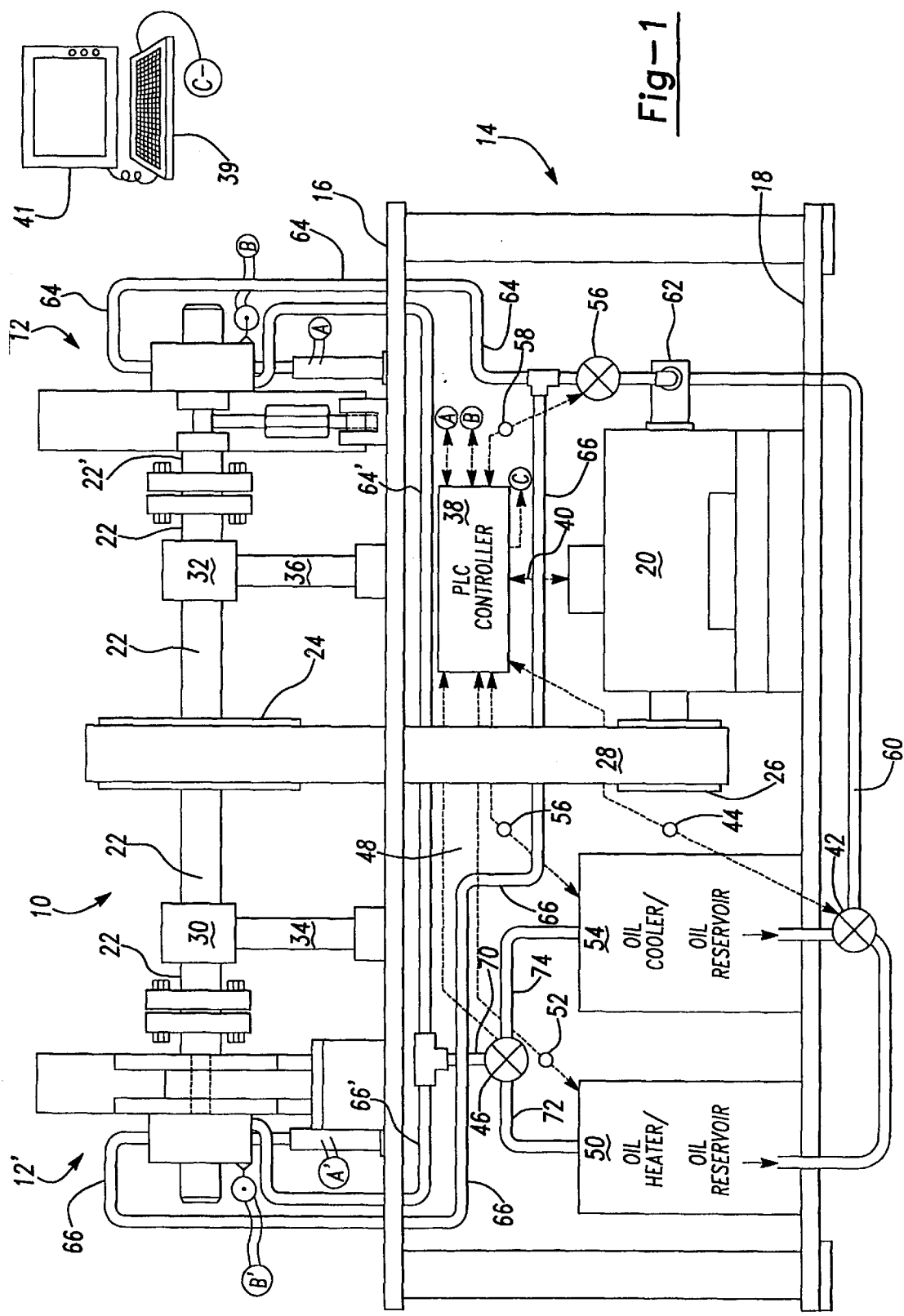
FIG. 1 is a diagrammatic view of the oil seal test machine of the present invention.

Oil seal test machine 10 includes, in part, left and right oil seal head assemblies 12', 12. Assemblies 12, 12' are identical in every way, and accordingly, only the constituent parts of right oil seal head assembly 12 will be discussed in detail here and after. It is to be assumed that all discussion of right oil seal head assembly 12 also applies to left oil seal head assembly 12'. Each oil seal assembly 12, 12' is capable of testing two oil seals at one time. Thus, oil seal test machine 10 is capable of testing a total of four oil seals at one time.

Table 14 is used to support oil seal test machine 10. Table 14 preferably includes upper surface 16 and lower surface 18. Electric motor 20 is used as the prime mover within oil seal test machine 10 and is responsible for rotating shaft 22. Motor 20 is connected to rotating shaft 22 by way of pulleys 24, 26 and belt 28. Any other conventional drive system could be used such as a direct drive, gears, chain, etc.

Shaft 22 is supported by mid shaft bearings 30, 32, which are in turn supported on surface 16 by way of stanchions 34, 36 respectively.

PLC Controller 38 interfaces with the various components of oil seal test machine 10 and provides the primary means whereby an operator can control an oil seal test. In a preferred embodiment, PLC Controller is provided with input/output (hereinafter I/O) Port C which interfaces to video monitor 41 and keyboard 39. The video monitor is the primary means whereby the test operator accesses the results of the various tests and the keyboard is the primary means whereby the operator selects various test options and otherwise controls the oil seal tests. Although video monitor 41 and a keyboard 39 are the preferred means of interface between oil seal test machine 10 and an operator, other I/O techniques can be used including a simple control panel which provides the operator with a predetermined number of switches to command the various operations performed by oil seal test machine 10 and a strip chart recorder or other recording device for conveying the results of an oil seal test.

The primary tasks performed by PLC Controller 38 are as follows:

1. to command an/or control the speed of motor 20 by way of control line 40,
2. to control oil output selection valve 42 by way of control line 44,
3. to control oil drain valve 46 by way of control line 48,
4. to control the temperature of oil heater/oil reservoir 50 by way of control line 52,
5. to control the temperature of oil cooler/oil reservoir 54 by way of control line 56,
6. and to control oil flow valve 56 by way of control line 58.

One important feature of oil seal test machine 10 is its ability to apply oil having a predetermined temperature to the seal being tested. In it's preferred embodiment the oil seal tester of the present invention has the ability to apply preheated or precooled oil in the range of 32° F. to 320° F. to the seal being tested. If the operator has commanded that the oil to be applied in the test will have a temperature below that of ambient temperature, PLC controller 38 will select the position of valve 42 such that the oil from oil cooler 54 is allowed to pass into pipe 60 and the oil from oil heater 50 is not allowed to pass into pipe 60. PLC controller 38 will then issue the proper commands to oil cooler 54 such that oil cooler 54 will maintain the temperature of the oil within oil cooler/oil reservoir 54 at the predetermined temperature. Oil pump 62 is driven by its own motor (not shown) and pressurizes lines 64, 66 to deliver oil continuously to right and left oil seal head assemblies 12, 12'.

Oil drain valve 46 can operate in two modes. It can open the flow of oil from line 70 to line 72 while keeping line 74 closed. Likewise it can conduct oil flow through line 70 to 74 while maintaining line 72 closed.

A continuous flow of oil is directed to right and left oil seal head assemblies 12, 12' by opening valve 56 and presetting valve 46 to conduct flow either to line 72 from line 70 or to line 74 from line 70. This continuous flow of oil will ensure that the oil seal being tested is constantly exposed to an oil having a predetermined temperature.

The oil control schemes elaborated above can be performed under direct program control of PLC Controller 38 wherein a software program has been loaded into the memory of PLC Controller 38 or under direct real time command of the operator who enters commands to PLC Controller 38 by way of keyboard 39. The various software programs and programming techniques which can be used to program PLC Controller 38 are not elaborated herein inasmuch as they are well known to those skilled in the art of PLC programming.

Figure 2D:
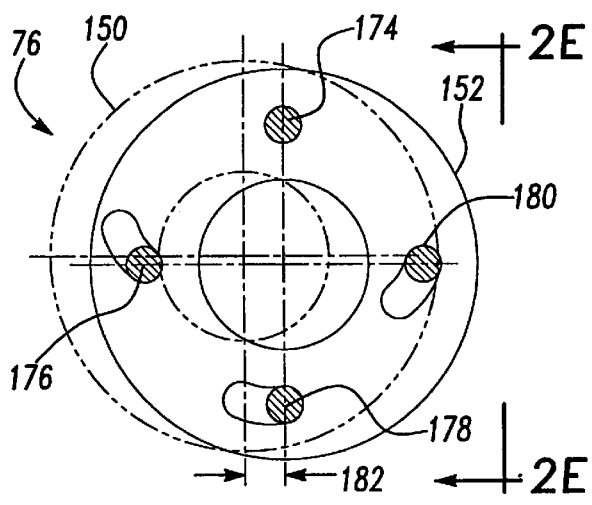
FIG. 2D is an enlarged view of encircled portion D of FIG. 2A.

Now referring to FIG. 2A, oil seal head assembly 12 is comprised of base plate 70, seal mounting housing 72, shaft to bore misalignment (hereinafter STBM) apparatus 74, shaft run out misalignment apparatus 76, reaction torque measurement 78, and fluid leak device detection apparatus 80.

Seal Base Plate and Seal Mounting Housing

Seal mounting housing 72 includes upper and lower openings 82, 84 respectively and inner and outer seal receiving bores 86, 88 (see FIG. 2C). Each of the seal receiving bores 86, 88 are sized to receive a respectively associated seal 90, 92 for testing in oil seal test machine 10. Upper opening 82 provides an ingress for fluid from line 64 into the inner chamber 94 of seal mounting housing 72. Lower opening 84 provides egress for oil within inner chamber 94 upon the opening of valve 46. Bores 86, 88 are sized to snugly receive seals 90, 92 respectively thereby providing a non-leak interface between their respective engaging surfaces.

Once seals 90, 92 are pressed into their respectively associated bores 86, 88, seal mounting housing 72 is slid into cylindrical portion 96 of base plate 70.

Now referring to FIGS. 2A and 2B, once seal mounting housing 72 is located sufficiently deep within cylindrical portion 96 of base plate 70, the outer cylindrical surface of seal mounting housing is supported by a plurality of rotating members 98–108. Rotating members 98–108 (see rotating member 98 set forth in FIG. 2B) include a wheel 112 and an axle 114. Axle 114 is fastened to inner web 110 of cylindrical portion 96. Wheel 112 freely rotates about axle 114. Preferably, rotating members 104, 106, and 108 all reside in the same plane and are generally spaced 116 in a 120° relationship to one another. Likewise, rotating members 98, 100, and 102 are also located in a common plane and are spaced in a 120° relationship to each other.

Although rotating members 98–108 provide the load bearing capacity to support the weight of seal mounting housing 72 and the weight of seals 90, 92, they do not provide a fluid sealing barrier. This fluid sealing barrier is provided by the presence of sealing rings placed adjacent inner webs 100, 111. The sealing ability of the sealing rings is enhanced by utilizing pressurized air 122 delivered to chamber 124. Chamber 124 is defined by sealing rings 118, 120 outer surface 126 of seal mounting housing 72 and inner web 110. The detail of this sealing arrangement for inner web 110 is shown in FIG. 2B. The identical arrangement is duplicated for web 111 (not shown in detail).

When chamber 124 is pressurized with pressurized air 122, a small amount of air 128 passes between sealing ring 118 and outer surface 126 of seal mounting housing 72. Likewise, a small amount of pressurized air 130 passes between sealing ring 120 and outer surface 126 of seal mounting housing 72. This air passage 128, 130 provides an excellent fluid tight seal preventing fluid 132 from leaking between sealing rings 118, 120 and outer surface 126 of seal mounting housing 72. Also, the presence of air flow between sealing rings 118, 120 and seal mounting housing 72 literally floats the mounting house on a blanket of air and causes it to move away from the adjacent surfaces of sealing rings 118, 120. This eliminates direct physical contact between sealing rings 118, 120 and mounting housing 72 which, in turn, eliminates virtually any error which would be introduced to the torque measured by reaction torque measurement apparatus 78 by the presence of friction.

Shaft To Bore Misalignment Apparatus

Shaft to bore misalignment apparatus 74 is comprised of threaded rod 132 which engages, at one end 134, ear 136 which extends from base plate 70. At an opposite end of base plate 70, a second ear extends therefrom and is pivotally mounted to referenced surface 140. When threaded rod 132 is rotated 142, it moves ear 136 parallel to linear path 144 thereby causing the center axis 147 of elastic annulus 146, 148 to become misaligned with shaft 22'. The ability of machine 10 to alter the shaft to bore misalignment is an important aspect of the present invention because it often is the case in actual vehicle applications that some degree of shaft to bore misalignment is present or will develop over time. By being able to adjust the shaft to bore misalignment of oil seal test machine 10, the extreme limits of seal tolerance and durability against this condition can be tested. It also is important to note that shaft to bore misalignment apparatus 74 can be adjusted while shaft 22' is rotating. Thus this adjustment can be effected without stopping or otherwise disturbing an on going seal test Shaft Run Out Misalignment Apparatus Now referring to FIGS. 2A and 2D, under actual use conditions, seals of the type envisioned for testing by oil seal test machine 10 must often tolerate some amount of shaft run out. Shaft run out can generally be defined by the misalignment between the geometrical center of a shaft and its axis of rotation. In order to impart this type of misalignment to shaft 22, shaft 22 is fastened to its respectively associated flange 150. Likewise, shaft 22' is fastened to its respectively associated flange 152. Flanges 150, 152 are preferably fastened to their respective associated shafts 20, 22' by way of welding or the like.

Figure 2E:
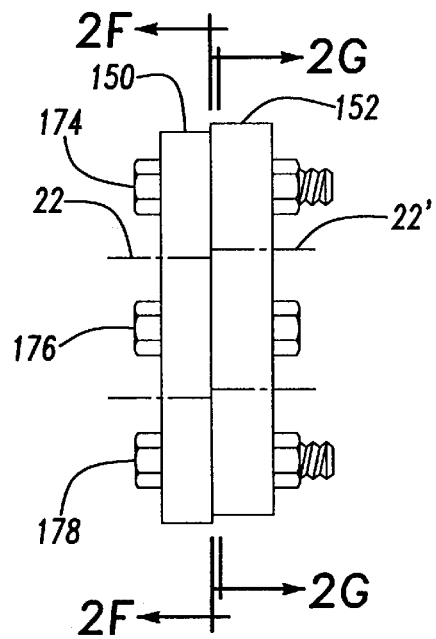
FIG. 2E is a cross sectional view taken substantially along lines E—E of FIG. 2D.
Figure 2F:
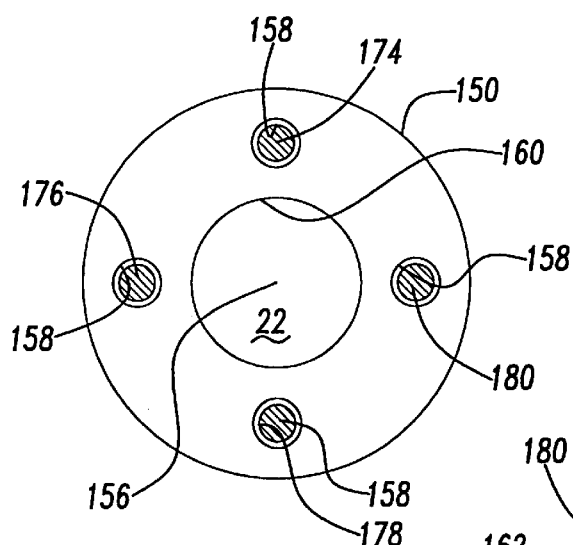
FIG. 2F is a cross sectional view taken substantially along lines F—F of FIG. 2E.
Figure 2G:
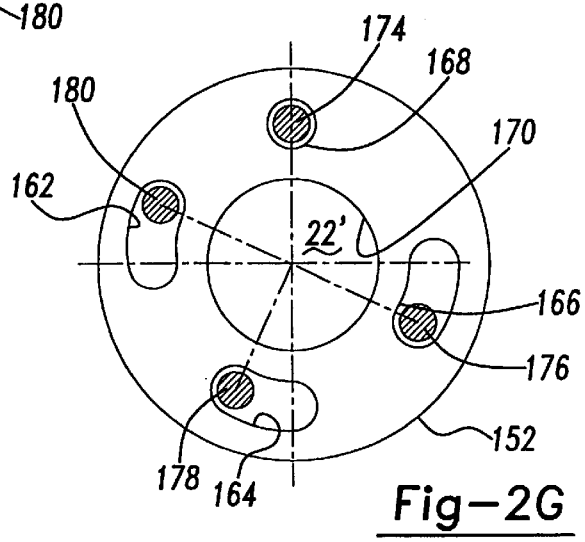
FIG. 2G is a partial cross sectional view of taken substantially along lines G—G of FIG. 2E.

Center point 156 is perfectly centered between openings 158 and opening 160 of flange 150. In contrast, flange 152 includes elongated bolt holes 162–166. Bolt hole 168 is not elongated. Opening 170 of flange 152 provides the opening for excepting shaft 22'. It is understood from this arrangement that when flanges 150, 152 are assembled as shown in FIG. 2A that the shaft run out of shaft 22' can be adjusted simply by loosening fasteners 174–180 (see FIG. 2E, fastener 180 not shown) and rotating flange 152 relative to flange 150. If flange 152 is rotated to its far most counter-clockwise position, the shaft run out misalignment is maximized 182. Unlike the shaft to bore misalignment, which can be adjusted without interrupting an ongoing test, the shaft run out misalignment cannot be so adjusted and the rotation of shaft 22 must be stopped in order to loosen fasteners 170–180 and rotate flange 150 relative to flange 152.

Reaction Torque Measurement Apparatus

Reaction torque measurement apparatus 78 is depicted as a strain gauge load cell having one end connected to seal mounting housing 72 and the opposite end anchored to reference surface 140. Because of the frictional engagement between sealing surface 182 (see FIG. 2B) of seal 90 against shaft 22', a reaction torque is exerted by shaft 22' against seal mounting housing 72 through seal 90. It is envisioned that for some seal tests, monitoring this friction over a predetermined period of time may give valuable information to the engineer as to the rate of wear of sealing surface 182. The reaction torque signal is transmitted along conductor B and in the embodiment set out herein it is presented to PLC Controller for displaying on display terminal 41. Of course, as has already been discussed, such a signal may be presented to a strip chart recorder for printout or may simply be directly displayed by analog or digital instrumentation. In a simplified embodiment of the present invention, the reaction torque exerted by shaft 22' onto seal mounting housing 72 may be read directly by way of a mechanical reaction arm fastened to seal mounting housing 72.

Fluid Detection Apparatus

In a first embodiment, the fluid detection apparatus 80 is simply comprised of a graduated cylinder 184 which is calibrated in volumetric units and can be used to collect the oil which escapes past sealing surface 182 and allows for a direct measure of its volume. In a second embodiment, a photo detector or other like electronic instrument is fastened below seal mounting housing 72 such that each time a drop of oil falls from seal mounting housing 72, the photo electric eye assembly 186, 188 detects such a droplet and an electrical signal is sent along cable A PLC Controller 38. PLC Controller 38 can be programmed to transfer count information to display terminal 41 regarding how many drops have been collected into graduated sealer 184 or, less sophisticated display means can be used such as mechanical counters or the like. In a preferred embodiment, both graduated cylinder 184 and photoelectric eye assembly 186, 188 are used in combination to determine the "leakyness" of the seals being tested.

The foregoing detailed description shows that the preferred embodiments of the present invention are well suited to fulfill the objects of the invention. It is recognized that those skilled in the art may make various modifications or additions to the preferred embodiments chosen here to illustrate the present invention, without departing from the spirit of the present invention. Accordingly, it is to be understood that the subject matter sought to be afforded protection hereby should be deemed to extend to the subject matter defined in the appended claims, including all fair equivalence thereof.

We claim:

1. An oil seal tester, comprising:

a moving shaft for engaging an oil sealing surface of an oil seal, at least one source of fluid to be applied against the moving shaft and against a first side of said oil seal, a force measuring device for measuring the force imparted to said oil seal from said moving shaft;

a seal mounting housing for securing said oil seal; and a base plate having at least two rotating members for rotatingly coupling the seal mounting house to the base plate, wherein said base plate includes at least one sealing ring encircling an outside perimeter of said seal mounting housing for forming a low friction fluid seal between said base plate and said seal mounting housing.

2. The oil seal tester of claim 1 wherein said moving shaft includes a rotating shaft.

3. The oil seal tester of claim 2, wherein said force measuring device includes a torque meter.

4. The oil seal tester of claim 1, further including means for heating said fluid contained in said at least one source of fluid.

5. The oil seal tester of claim 1, further including an oil cooler for cooling said fluid contained in said at least one source of fluid.

6. The oil seal tester of claim 1, wherein said moving shaft is a rotating shaft and wherein said oil seal tester further includes an offset flange coupling coupled to said moving shaft for altering the run out of said rotating shaft.

7. The oil seal tester of claim 1, further including a shaft to bore misalignment coupling coupled to said oil seal for offsetting a center axis of said oil seal from a center of said shaft.

8. The oil seal tester of claim 1, including means for detecting the passage of fluid beyond the sealing surface of said seal.

9. The oil seal tester of claim 1, wherein said base plate includes air chambers for passing pressurized air adjacent said sealing ring.

10. The oil seal tester of claim 9, wherein said sealing ring is made at least in part from Teflon.

11. The oil seal test of claim 1, wherein said at least one source of fluid includes a first fluid source maintained at a first temperature and a second fluid source maintained at a second temperature.

12. The oil seal tester of claim 11, further including means for selecting between said first and second fluid sources.

13. An oil seal tester, comprising:

a moving shaft for engaging an oil sealing surface of an oil seal, at least one source of fluid to be applied against the moving shaft and against a first side of said oil seal, a force measuring device for measuring the force imparted to said oil seal from said moving shaft;

a base plate;

a seal mounting housing for securing said oil seal disposed within said base plate; and at least two rotating members in simultaneous contact with said seal mounting housing and said base plate to permit selective rotation of said housing with respect to said base plate.

14. The oil seal tester of claim 1, wherein said base plate includes an inner surface and said housing includes an outer surface, said rotating members disposed between said inner and outer surfaces.

15. The oil seal tester of claim 13, wherein said base plate includes an inner surface and said housing includes an outer surface, said rotating members disposed between said inner and outer surfaces.

* * * * *